United States Patent [19]

Furukawa et al.

[11] 4,217,548
[45] Aug. 12, 1980

[54] FLAW DETECTOR FOR PIPE EMPLOYING MAGNETS LOCATED OUTSIDE THE PIPE AND DETECTOR MOUNTED INSIDE AND MOVABLE ALONG THE PIPE WITH THE MAGNETS

[75] Inventors: Yasuyuki Furukawa; Yoshihisa Fujii; Hitoshi Tanaka, all of Wakayama; Tetsuya Hirota, Amagasaki, all of Japan

[73] Assignee: Sumitomo Kinzoku Kogyo Kabushiki Kaisha, Osaka, Japan

[21] Appl. No.: 968,703

[22] Filed: Dec. 12, 1978

Related U.S. Application Data

[63] Continuation-in-part of Ser. No. 809,829, Jun. 24, 1977, abandoned.

[51] Int. Cl.² ........................................... G01R 33/12
[52] U.S. Cl. .................................. 324/220; 324/242
[58] Field of Search ............................. 324/219–220, 324/226, 227, 228

[56]  References Cited
U.S. PATENT DOCUMENTS

| 1,978,252 | 10/1934 | Drake | 324/241 |
| 2,308,159 | 1/1943 | Drummond et al. | 324/220 |
| 2,563,254 | 8/1951 | Lewis | 324/229 |
| 3,209,243 | 9/1965 | Walters et al. | 324/220 |
| 3,535,623 | 10/1970 | Wood et al. | 324/220 |
| 3,693,075 | 9/1972 | Förster | 324/220 |
| 3,872,378 | 3/1975 | Shirawa et al. | 324/226 |

Primary Examiner—Rudolph V. Rolinec
Assistant Examiner—Walter E. Snow
Attorney, Agent, or Firm—Ladas, Parry, Von Gehr, Goldsmith & Deschamps

[57]  ABSTRACT

A detector for magnetically detecting flaws on the inner surface of a pipe of magnetizable material comprises a magnetizing assembly having exciting magnets and movable longitudinally along the exterior of the pipe and a detecting assembly movable longitudinally along the interior of the pipe. The magnetizing and detecting assemblies are opposite and close to each other through the wall of the pipe and movable longitudinally of the pipe in a synchronized manner to ensure highly accurate flaw detection.

5 Claims, 15 Drawing Figures

FLAW DETECTOR FOR PIPE EMPLOYING MAGNETS LOCATED OUTSIDE THE PIPE AND DETECTOR MOUNTED INSIDE AND MOVABLE ALONG THE PIPE WITH THE MAGNETS

CROSS REFERENCE TO RELATED APPLICATION

This is a continuation-in-part application of U.S. application Ser. No. 809,829, filed June 24, 1977 and entitled MAGNETIC INSPECTION METHOD AND APPARATUS FOR INNER SURFACE OF PIPE, now abandoned.

BACKGROUND OF THE INVENTION

This invention relates to magnetic flaw detecting method and apparatus for inspecting inner surface of steel pipes, especially suitable for the inspection of elongated steel pipes with relatively small diameters.

The present inventors have long been engaged in the research and development of the magnetic flaw detectors for detecting flaws present on the outer surfaces of slubs or round steel bars or flaws present on the outer or inner surfaces of steel pipes. The known magnetic flaw detectors operate on similar principles, in which a strong magnetic field is produced by exciting magnets on a surface to be inspected and a magneto-sensitive element is placed in the magnetic field thus produced to detect a magnetic flux which leaks from a flaw which may present on the surface under inspection.

For inspecting inner surfaces of a steel pipe, there have been known two types of magnetic flaw detection systems, i.e. an internal type in which a head assembly mounting a magnetizer and a detector is inserted into the steel pipe and moved along the inner surfaces thereof and an external type in which a similar head assembly is moved along the outer surfaces of the pipe. However, the prior art magnetic flaw detection methods and apparatus of this sort have inherent drawbacks. More particularly, the internal type in which the head assembly has to be inserted into the pipe is limited to those pipes which have a large diameter (over 300 mm in inside diameter, while the external type is applicable to pipes of relatively small diameters but poor in detecting ability.

It is therefore a primary object of the present invention to provide a magnetic flaw detector which is capable of inspecting small-diameter and thick-walled pipes for detecting flaws on the entire area of the inner wall surfaces of the pipes with high detecting efficiency and ability.

It is another object of the present invention to provide a magnetic flaw detector which can follow undulations on the inner surfaces of a pipe to perform flaw detection of high reliability and precision.

It is still another object of the present invention to provide a magnetic flaw detector which can scan the surfaces to be inspected in a reliable manner and stable conditions.

SUMMARY OF THE INVENTION

According to the present invention, there is provide a magnetic flaw detector for inspecting inner wall surfaces of a pipe of magnetizable material, the detector comprising: a support rod mounted on a wheeled carriage which is movable along a rail, the support rod having a hollow space at least in the fore end portion thereof to be inserted into the pipe and a window formed in the fore end portion to open toward an inspecting spot on the inner wall surface of the pipe; a detector assembly having a base plate accommodated within the hollow space at the fore end of the support rod and movable radially of the support rod, a plural number of detecting members mounted on the base plate in alignment in the longitudinal direction of the support rod, each one of the detecting members having magneto-sensitive element urged by respective biasing means to project independently through the window toward the inner wall surface of the pipe, and a plural number of guide rollers mounted on the base plate and adapted to be brought into rolling contact with the inner wall surface of the pipe to support the base plate when the detecting members are abutted against the inner wall surface of the pipe; a guide mechanism having a support frame attached to the distal end of the support rod and swingable outwardly in a direction opposite to the projecting direction of the magneto-sensitive elements, and a guide roller adapted to be brought into rolling contact with the inner wall surface of the pipe to support the support rod when the support frame is swung out; a magnetizing assembly having a magnetizing head mounted on a wheeled carriage movable with the first-mentioned wheeled carriage to move the magnetizing head longitudinally along the outer wall surface of the pipe, exciting magnets mounted on the magnetizing head in a position closely opposing the magneto-sensitive elements across the wall of the pipe, and follower rollers adapted to be brought into rolling contact with the outer wall surface of the pipe to support the exciting magnets in an operating position close to the outer wall surface of the pipe; and means for rotating the inspecting pipe about the axis thereof during the flaw detecting operation by the detecting and magnetizing assemblies.

The above and other objects, features and advantages of the invention will become apparent from the following description and the appended claims, taken in conjunction with the accompanying drawings which show by way of example preferred embodiments of the present invention.

DESCRIPTION OF PREFERRED EMBODIMENTS

Figure 1:
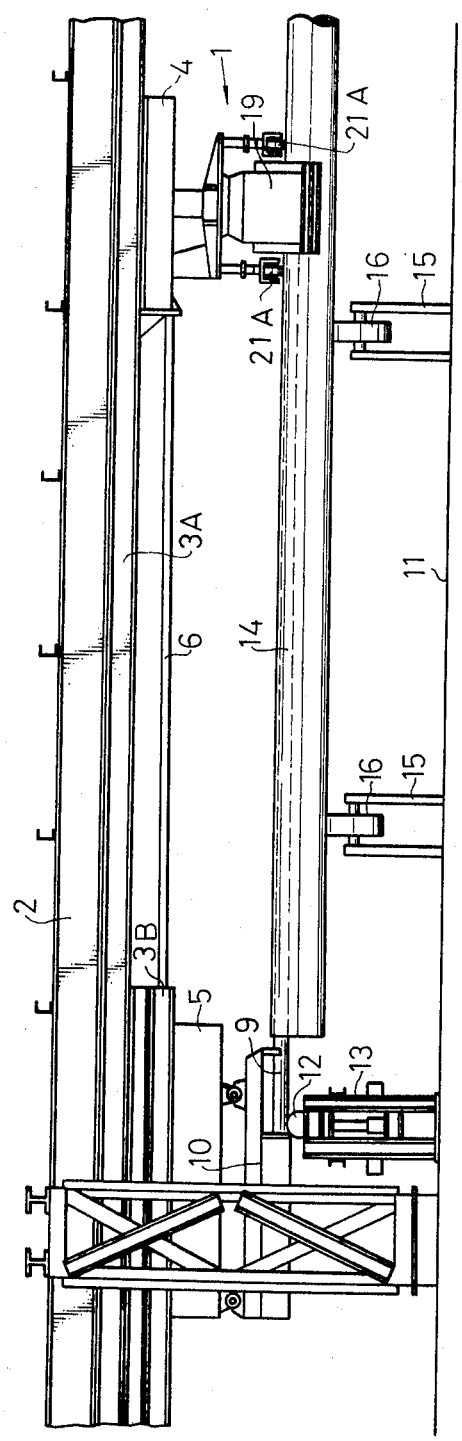
FIG. 1 is a diagrammatic side view of a magnetic flow detector for inspecting the inner wall surfaces of a pipe according to the present invention.
Figure 2:
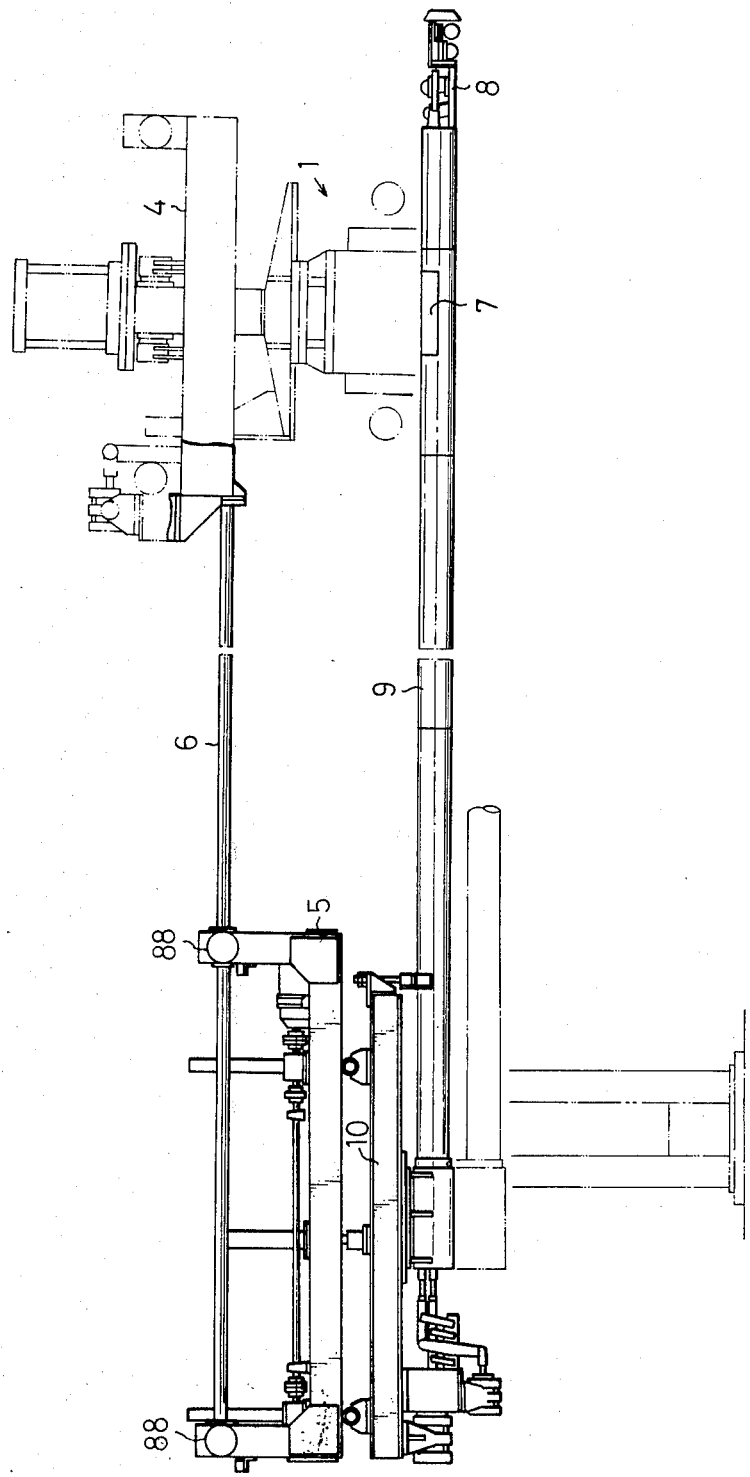
FIG. 2 is a diagrammatic side view of a magnetizer assembly and a support rod of a detector assembly shown in FIG. 1, showing the manner in which the support rod is supported.

Referring to FIGS. 1 and 2, there is diagrammatically shown the magnetic flaw detector which is adapted to inspect inner wall surfaces of a pipe according to the present invention. The magnetic flaw detector largely consists of a magnetizer assembly 1 which is movable longitudinally along the outer surfaces of the pipe to be inspected and a detector assembly 7 which is movable longitudinally along the inner surfaces of the pipe in synchronism with the magnetizer assembly 1. The magnetizer assembly 1 is supported pendant from a wheeled carriage 4 which is movable along rails 3A which is mounted on a beam of frame 2. The carriage 4 is locked through a connecting rod 6 to another wheeled carriage 5 which is movable along rails 3B. Suspended from the carriage 5 is a vertically movable support assembly 10 which is detachably connected to a horizontally extending support rod 9 which supports the detection assembly 7 and a guide mechanism 8 on the tip end portion thereof.

The support rod 9 is movably supported on a roller 12 which is mounted on a base frame 13 fixed on the floor 11 immediately beneath the rails 3A and 3B.

A steel pipe 14 to be inspected is placed on turning rollers 16 which are mounted on brackets 15 immediately beneath the rail 3A and rotatingly driven from suitable means. While the steel pipe 14 is rotated by the turning rollers 16, the support rod 9 with the detecting assembly 7 and guide mechanism 8 is inserted thereinto and at the same time the magnetizing head assembly 1 is moved along the outer surfaces of the steel pipe 14, so that the detecting assembly 7 and the magnetizing assembly 1 advance helically along the wall of the pipe 14 to scan the entire area of the inner surfaces thereof. For travels along the rails 3A, the wheeled carriages 4 and 5 are connected to a chain or cable which is driven from a motor or other suitable means.

Figure 3:
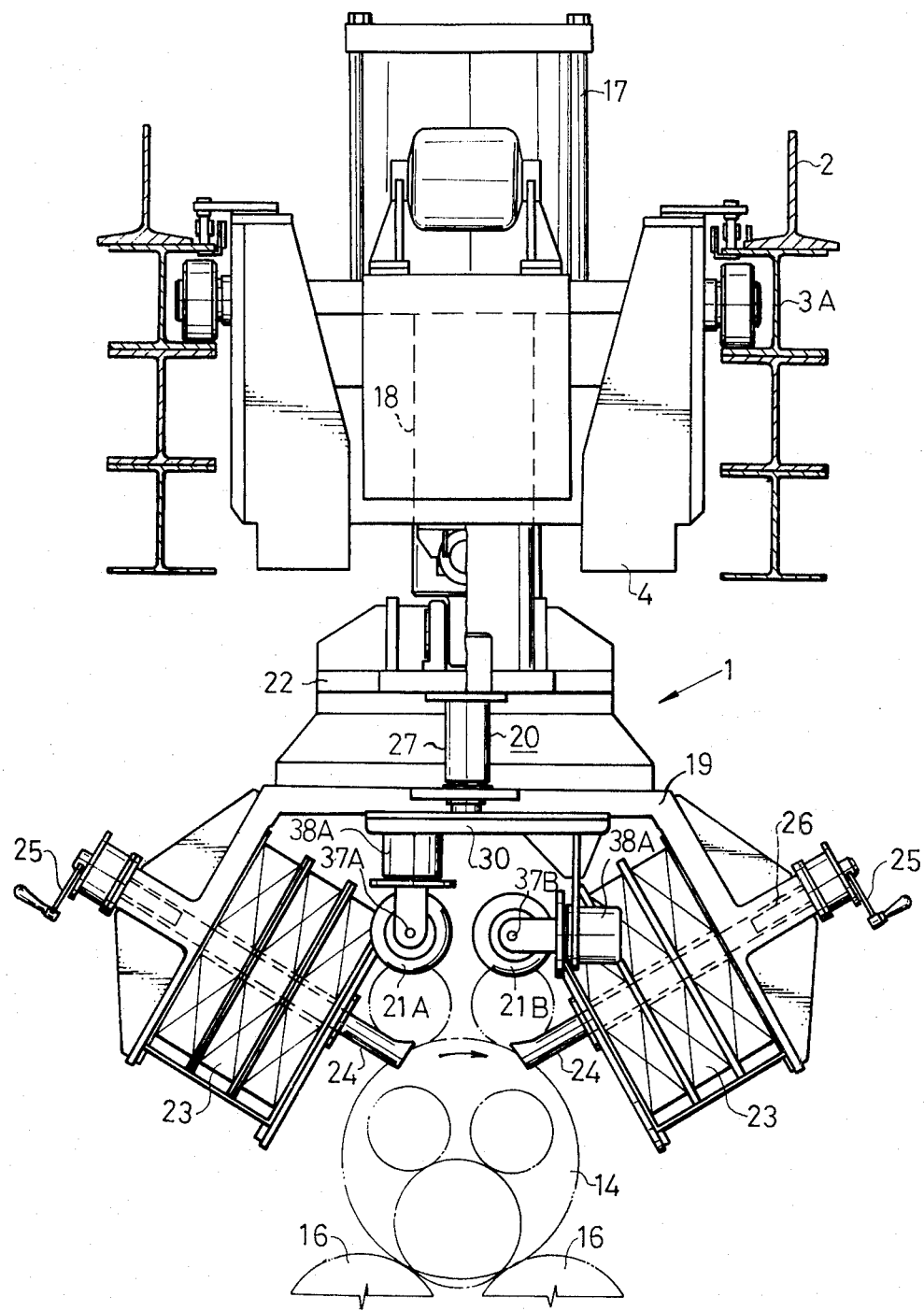
FIG. 3 is a diagrammatic front view of the magnetizer assembly.
Figure 4:
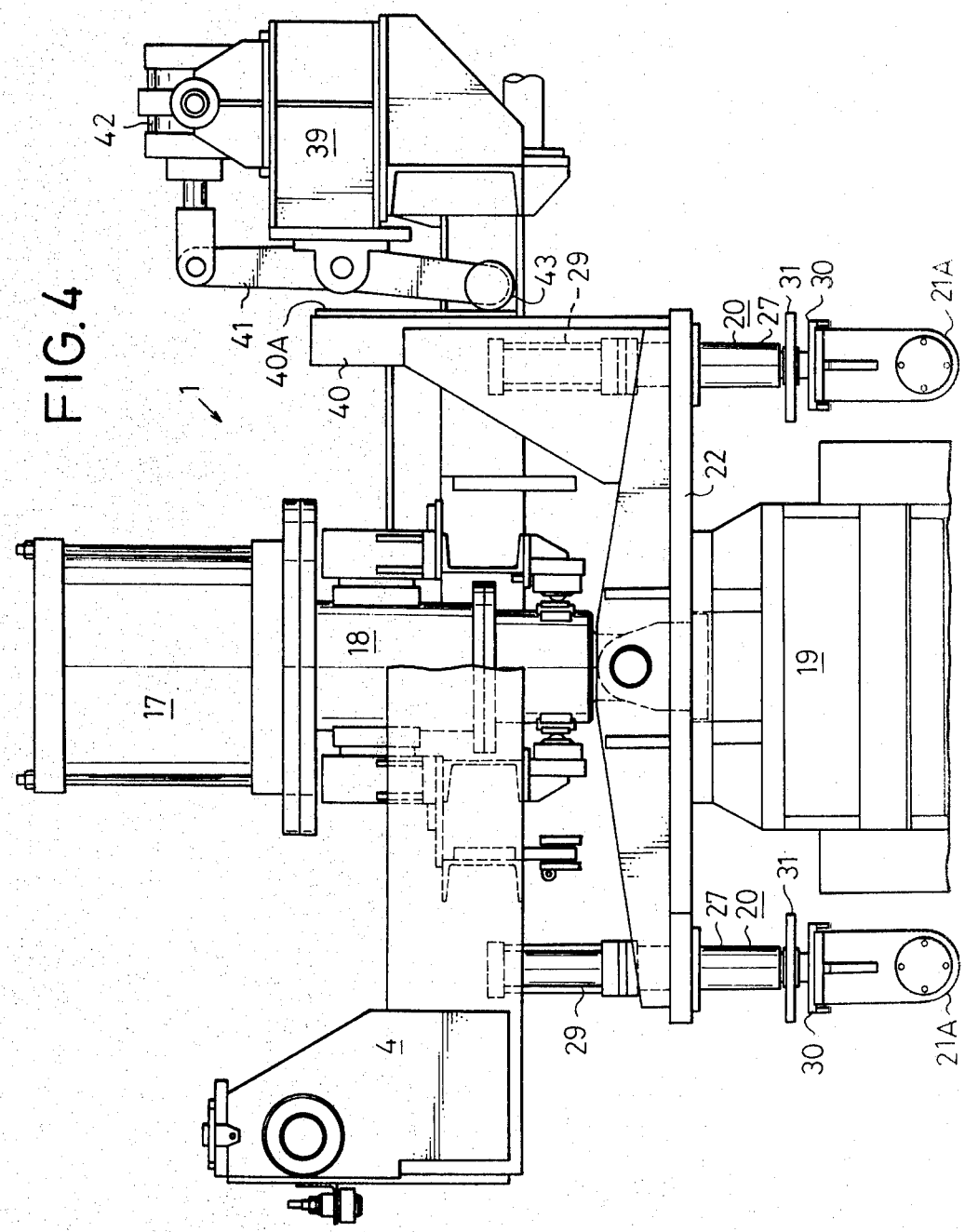
FIG. 4 is a diagrammatic side view of the magnetizer assembly.

Referring to FIGS. 3 and 4, the magnetizing assembly 1 is provided with a magnetizing head 19 which is pivotally supported at the lower end of a vertical shaft 18 which is movable up and down by operation of a cylinder 17 on the wheeled carriage 4. Provided on the front and rear sides of the magnetizing head 19 are follower rollers 21A and 21B which are movable up and down by operation of a lift mechanism 20. The lift mechanism 20 is mounted through a plate 22 which is fixedly mounted at the upper end of the magnetizing head 19 to extend forward and rearward thereof.

The magnetizing head 19 has a pair of exciting magnets 24 arranged in V-fashion each extending through a coil 23. The exciting magnets 24 are placed symmetrically on opposite sides of a spot under inspection of the steel pipe 14. The rear end of each exciting magnet 24 is threaded into a threaded shaft 26 with a handle 25 so that the lower reach of the exciting magnet 24 can be adjusted by turning the handle 25.

Figure 5:
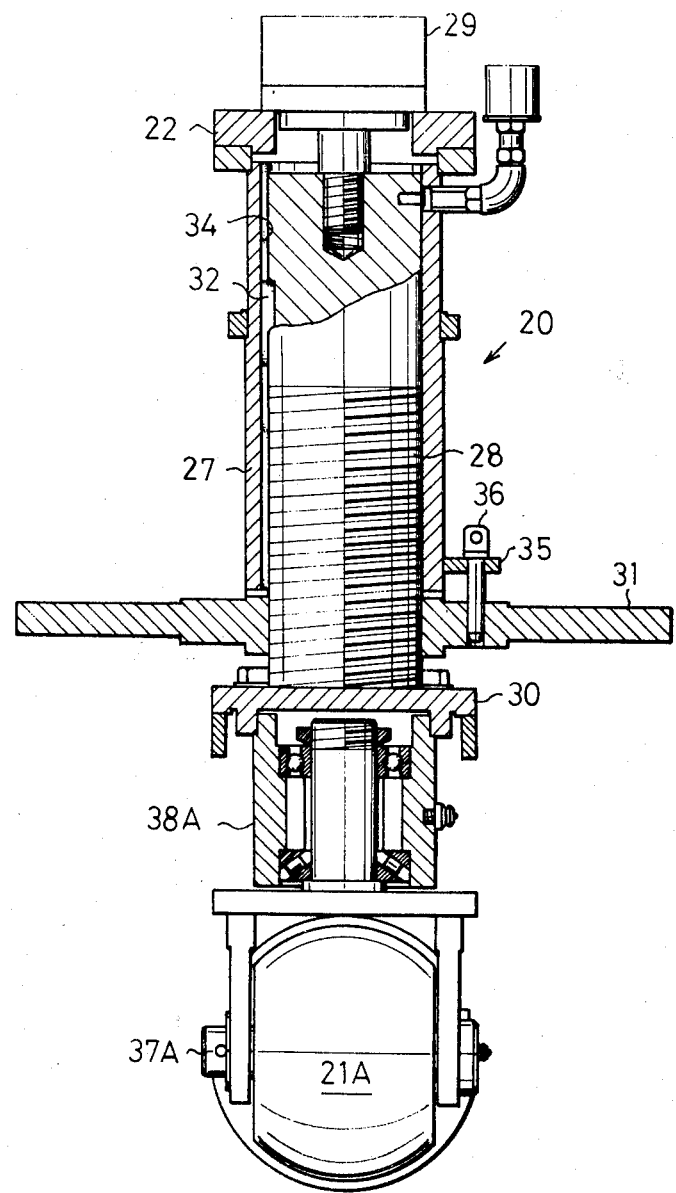
FIG. 5 is a diagrammatic longitudinal cross-section of a follower roller lift mechanism of the magnetizer assembly.

As shown particularly in FIG. 5, the lift mechanism 20 is provided with an open-bottomed sleeve 27 which is fixed to the underside of the plate 22, an externally threaded shaft 28 which is slidably fitted into the cylinder 27, and an upper cylinder 29 which is mounted on the plate 22 and operative to lift the shaft 28. A support plate 30 is fixed to the bottom of the shaft 28 to support the follower rollers 21A and 21B. Threaded on the shaft 28 is an annular disclike stopper 31 which is abutted against the lower end of the sleeve 27 to limit the upward movement of the shaft 29. When the magnetizing head 19 is brought to the circumference of the steel pipe 14, the follower rollers 21A and 21B are held in rolling contact with the circumferential surface of the steel pipe 14 to maintain the magnetizing head 19 in constant positional relation with the circumference of the steel pipe 14. In this instance, arrangements may be made such that the follower rollers 21A and 21B are supported solely by a cylinder 29 of a larger output. However, cylinders are generally difficult to make fine adjustment of the stroke, so that it is more practical to employ the stopper 31 for setting the positions of the follower rollers 21A and 21B. When adjusting the position of the roller 21A or 21B, it is necessary to turn the stopper 31 securely relative to the shaft 28. For this purpose, the shaft 28 is provided with a key 32 to block its rotation. The key 32 is guided by a vertical groove 34 on the inner periphery of the sleeve 27 when the shaft 28 is moved up and down within the sleeve 27. The sleeve 27 is provided at its lower end with a bracket 35 for receiving a stud pin 36 which blocks rotation of the stopper 31.

As shown in FIGS. 3 and 4, the follower rollers 21A and 21B are rotatably mounted on the respective shafts 37A and 31B which are rockably supported on bearing blocks 38A and 38B, respectively. Therefore, coupled with the rocking movements of the respective shafts 37A and 37B, the follower rollers 21A and 21B can follow any spiral or helical movement of any pitch along the steel pipe 14. The circumferential surfaces of the follower rollers 21A and 21B are formed spherically to ensure smooth rolling contact with the circumferential surfaces of the steel pipe 14.

As illustrated in FIG. 3, the shafts 37A and 37B of the follower rollers 21A and 21B are rockable in a horizontal plane and a vertical plane, respectively, while being fed rearwardly as seen in FIG. 3 along the steel pipe 14 which is being rotated clockwise. In FIG. 3, the follower roller 21A has its right-hand lower portion in contact with the circumference of the steel pipe 14 while the other follower roller 21B has its left-hand lower portion in contact with the steel pipe 14. The follower roller 21A is brought into rolling contact with the steel pipe 14 from the position of FIG. 3 without slipping when the shaft 37A is rocked through an angle less than 90 degrees as seen from beneath in FIG. 3. On the other hand, the follower roller 21B is brought into rolling contact with the steel pipe 14 from the position of FIG. 3 when the shaft 37B is rocked through an angle less than 90 degrees as seen from left in FIG. 3. Where the steel pipe 14 is put in counterclockwise rotation, the shafts 37A and 37B have to be turned in reverse directions in order to bring the follower rollers 21A and 21B into slip-free rolling contact with the steel pipe 14.

In contrast, the moments which occur to the shafts 37A and 37B according to the positions of the rolling contact on the steel pipe 14 and the feed direction of the follower rollers 21A and 21B act only in those directions. In other words, in order to follow the spiral movement smoothly, the rocking shafts have to be arranged perpendicular to each other with the follower rollers 21A and 21B in a particular positional relationship.

The exciting coil 23 is supplied with D.C. current to magnetize the steel pipe 14 sufficiently up to the inner surfaces thereof, so that flaws present within a depth of 5% of the wall thickness of the pipe may be detected.

Referring to FIG. 4, the wheeled carriage 4 has at its fore end a support mechanism 39 for supporting the plate 22 through an upright engaging member 40 which is provided on the plate 22. The support mechanism 39 has a rod of a cylinder 42 connected to an upper end of a vertically extending link 41 which is pivotally supported at its center portion. An engaging roller 43 is journalled at the lower end of the link 41 so that the roller 43 is pressed against the engaging member 40 when the link 41 is rocked by the operation of the cylinder 42. The engaging roller 43 is abutted against front side 40A of the engaging member 40 which faces the fore end of the wheeled carriage 4 to guide the upward or downward movement of the plate 22 without causing swaying movement thereto. This sort of support for the plate 22 is advantageous when supporting the magnetizing head 19 by one follower rollers 21A and 21B. In the flaw detection in general, the support rod 9 is fully inserted into the steel pipe 14 in the first place and then, while the support rod 9 is extracted from the steel pipe 14, magnetizing assembly 1 and the detecting assembly 7 are moved axially along the steel pipe 14 by retracting the wheeled carriage 4. Therefore, before the magnetizing assembly 1 reaches the end of the steel pipe 14, the follower rollers 21A and 21B at the rear end get off the circumference of the steel pipe 14, causing a counterclockwise moment, as seen in FIG. 4, to the plate 22 due to the reaction force received by the follower rollers 21A and 21B at the fore end. The engaging roller imparts to the plate 22 a moment which offsets the just-mentioned counterclockwise moment to block rocking motions of the plate 22, thereby preventing damages which would otherwise be caused to the magnetizing head 19 and maintaining the head 19 in constant positional relation with the circumference of the steel pipe 14. In addition, since the upward or downward movements of the plate 22 are guided by the engaging roller 43, the magnetizing head 19 can move up and down following any undulations which may present on the circumference of the steel pipe 14. In this instance, the cylinder 17 vertically movably supports the plate 22.

As shown in FIGS. 8 through 11, the detecting end assembly 7 is encased in a support rod 9 in the form of a hollow pipe and has a row of detecting members 46 mounted on a base plate 44, each having a magneto-sensitive element 45. A pair of guide rollers 47A and 47B are mounted on the base plate 44 at the opposite ends of the row of detecting members 46. The support rod 9 is provided with a window 48 on the upper side thereof to expose the row of magneto-sensitive elements 45 and the guide rollers 47A and 47B to the inner surface of the steel pipe 14.

Journalled on the underside of the base plate 44 is the fore end 49A of a rocking arm 49 to move the base plate 44 up and down. The base end portion 49B of the arm 49 is pivotally supported on a bracket 50 which is provided on the inner surface of the support rod 9, the base end portion 49B having an upwardly extending crank portion 49C the upper end of which is pivotally connected to a reciprocating rod 51. By the back and forth movements of the reciprocating rod 51, the crank 49c and therefore the arm 49 is rocked to push the base plate 44 upwardly toward the inner surface of the steel pipe 14. Whereupon, the guide rollers 47A and 47B are raised into abutting engagement with the inner surface of the steel pipe 14, and the detecting units 46 are held in contact with the inner surface of the steel pipe 14 under a suitable pressure which is controlled by the guide rollers 47A and 47B.

The bracket 50 and reciprocating rod 51 are interconnected by a link 52 which is disposed parallel to the crank portion 49c, allowing the reciprocating rod 51 to make horizontal movements only. The horizontal movements of the rod 51 is guided by a guide bush 53, which guide bush serves to ensure that the reciprocating rod 51 make the horizontal movements securely and smoothly.

An upwardly extending engaging member 54 is provided on the upper side of the base plate 44 at a position closer to the base end of the support rod. The inner side 54A of the engaging member 54 is abuttable against an engaging roller 56 which is journalled at the fore end of a horizontally extending base plate support rod 55. In this instance, if the engaging roller 56 is pressed against the surface 54A by suitably moving the base plate support rod 55 back and forth, the base plate 44 can be supported by the engaging roller 56 and the guide roller 47A alone. This arrangement is advantageous to the flaw detection at the end of the steel pipe 14 where the guide roller 47B cannot abut against the inner surface of the steel pipe 14. As mentioned hereinbefore, the support rod 9 is fully inserted into the steel pipe 14 before starting the flaw detection and then the detector members 46 are moved along the inner surfaces of the steel pipe 14 by extracting the support rod 9 therefrom. In this instance, before the detector members 46 reach the end of the steel pipe 14, the guide roller 47B comes out of the pipe 14. Therefore, if the base plate 44 is supported by the guide rollers 47A and 47B alone, it will be rotated clockwise in FIG. 8 or 9 as soon as the guide roller 47B comes out of the steel pipe 14, causing damages to the detector members 46 by pressing them forcibly against the inner surface of the steel pipe 14. In order to avoid this, the engaging roller 56 is caused to support the base plate 44 before the guide roller 47B leaves the steel pipe 14. By doing so, the base plate 44 can be supported stably after the guide roller 47B has come out of the steel pipe 14 during flaw detection at the end portion thereof.

The engaging roller 56 guides the engaging member 54 substantially in the vertical direction to allow upward or downward movements of the base plate 44. Therefore, when there are undulations on the inner surfaces of the steel pipe 14, the arm 49 moves the base plate 44 up and down to hold the guide rollers 47A and 47B constantly in contact with the inner surfaces of the pipe. In the event of the flaw detection at the end of the steel pipe 14, the holder roller 56 guides the base plate 44 in the vertical direction to make the detector members 46 follow the inner surfaces of the pipe, thus preventing turn-over of the base plate 44.

The base plate support rod 55 which is guided by the bush 57 in the horizontal direction is connected to the brackets 50 by parallel links 58 to ensure its smooth operation in a manner similar to the reciprocating rod 51.

The detector members 46 are aligned in the longitudinal direction of the support rod 9 to effect scanning covering a number of spots on the inner surface of the pipe. Therefore, almost the entire area of the inner wall surface of the pipe can be inspected very efficiently. As shown particularly in FIG. 9, each detector member 46 is upwardly urged by torsion coil spring 59 and thus independently movable to follow the undulations which may exist on the inner surface of the steel pipe 14, providing secure and accurate operation. In addition, the pressure of contact between the detector members 46 and the inner surface of the steel pipe 14 is maintained constant to protect the detector members 46 against damages.

Figure 13:
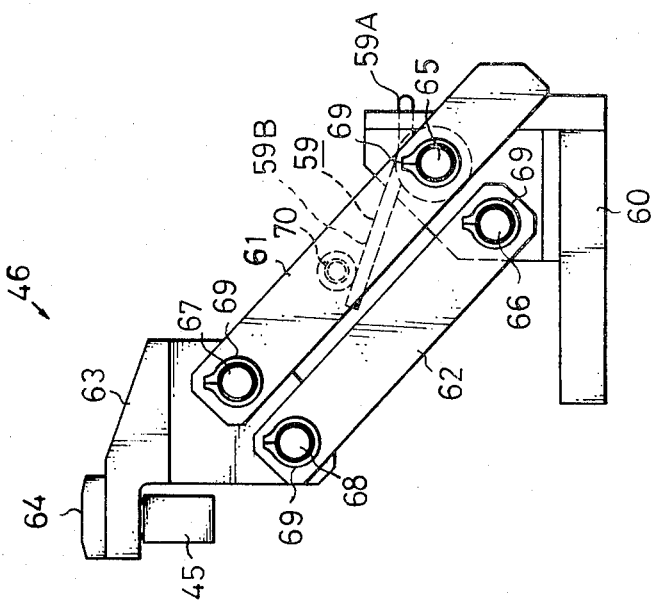
FIG. 13 is a right-hand side view of the detector assembly of FIG. 12.
Figure 12:
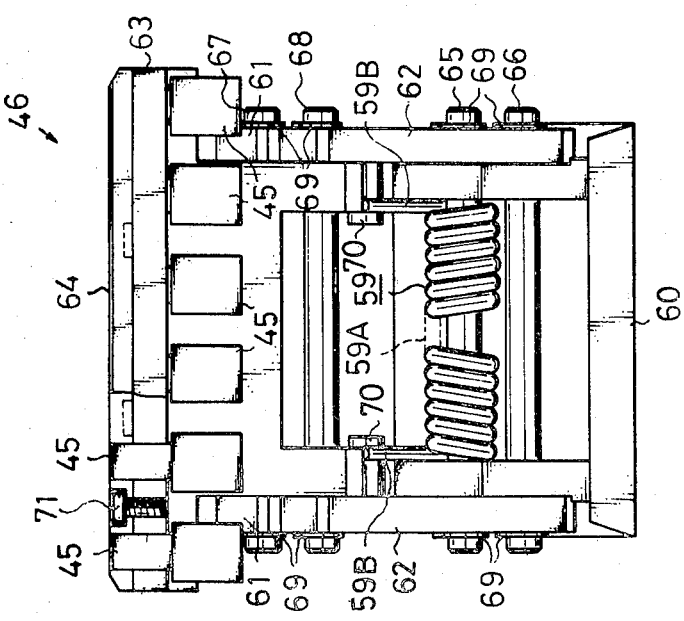
FIG. 12 is a diagrammatic view showing the detector assembly on an enlarged scale.

Referring to FIGS. 12 and 13, the detector member 46 is provided with a foot 60 which is fixedly mounted on the base plate 44, obliquely upwardly extending parallel links 61 and 62 one ends of which are pivotally connected to the foot portion 60, and a bouncing block 63 which is connected at opposite ends to the other ends of the links 61 and 62. The torsion coil spring 59 is mounted on the foot portion 60 in such a manner as to urge the links 61 and 62 upwardly. Therefore, the bouncing block 63 on follow the inner surface of the steel pipe 14, bouncing up and down parallel to the foot portion 60. The magneto-sensitive elements 45 are securely fitted across the bouncing block 63 with the projected upper ends of the respective magneto-sensitive elements 45 protected by a shoe 64. The shoe 64 is adhered to the upper surface of the bouncing block 63 to cover the upper end portions of the projected upper ends of the magneto-sensitive elements 45, and held in sliding contact with the inner surfaces of the steel pipe 14. While the shoe 64 is slided along the inner surface of the pipe 14, the magneto-sensitive elements 45 are maintained close enough to and at a constant distance from the inner surface of the steel pipe 14. The magneto-sensitive elements 45 are thus protected against damages in a manner which guarantees their reliable and accurate performance.

The links 61 and 62 are pivotally connected to the foot portion 60 by shafts 65 and 66 and to the bouncing block 63 by shafts 67 and 68. The shafts 65 to 68 are held in the respective positions by stop rings 69. The torsion coil spring 59 which is mounted on the shaft 65 has its center portion 59A held in the foot portion 60, with the opposite end portions 59A and 59B resiliently abutted against the undersides of pins 70 which are provided on the respective links 61. The shoe 64 is fixed to the bouncing block 63 by a screw 71.

Figure 11:
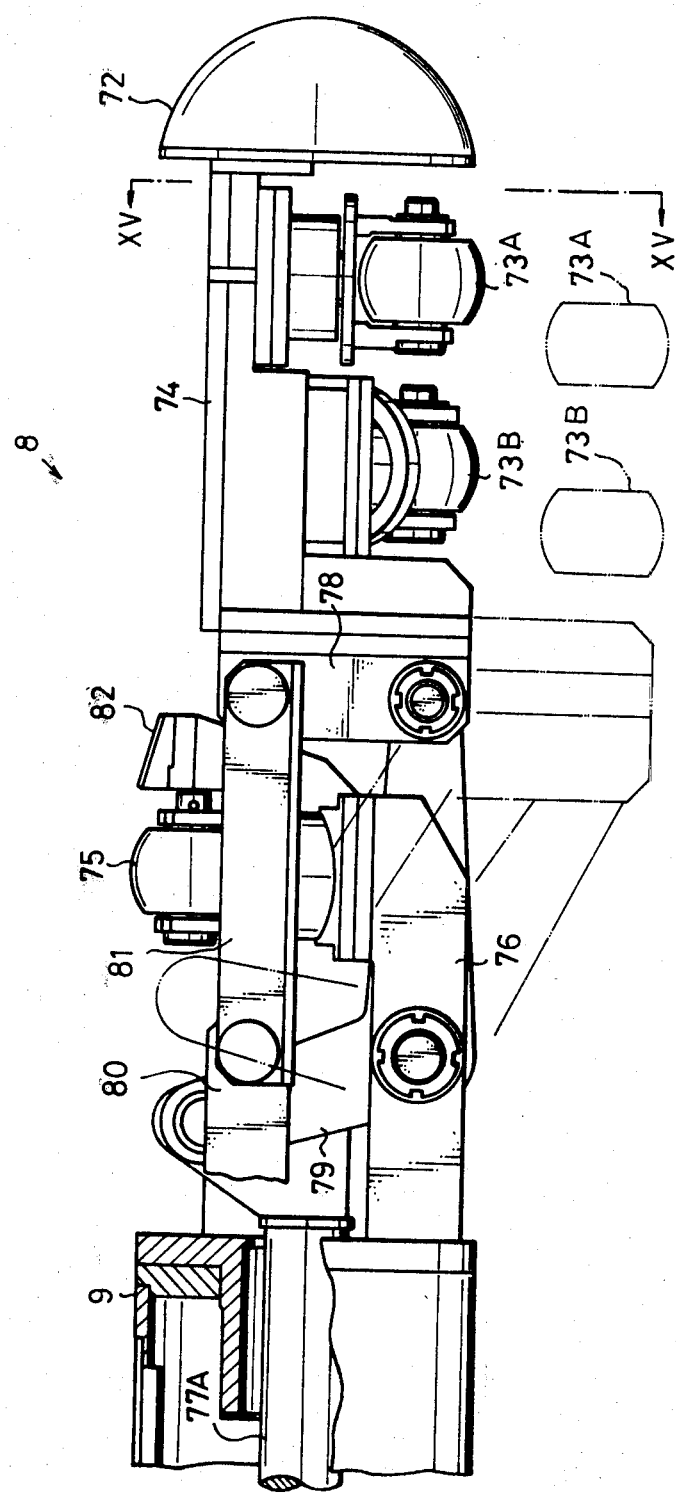
Figure 15:
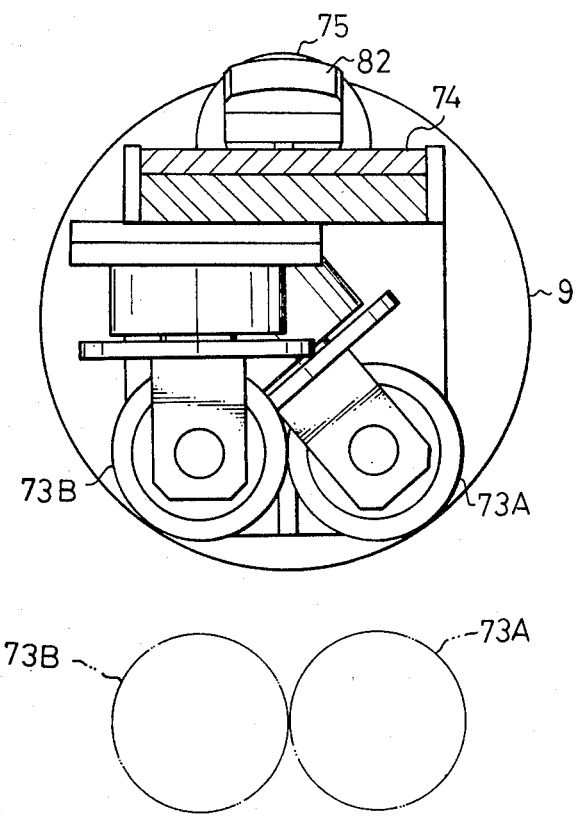
FIG. 15 is a diagrammatic cross-section taken on line XV—XV of FIG. 11.

Referring now to FIGS. 11 and 15, the aforementioned guide mechanism 8 is provided at the fore end of the support rod 9 and includes a semi-spherical or frusto-conical guide head 72 at the distal end of a support frame 74. On the support frame 74, there are mounted guide rollers 73A and 73B which are rotatable about the respective axes. Another guide roller 75 which is also rotatable about its axis is mounted on a bracket 76 which is secured to the fore end of the support rod 9 to extend toward the support frame 74. A bellcrank 79 the intermediate portion of which is pivotally supported on the bracket 76 has its one end pivotally connected to the rod 77A of a cylinder 77 which is provided within the support rod 9, with the other end of the bellcrank 79 pivotally connected to a bracket 78 of the support frame 74. A link arm 81 is provided parallel with the other end of the bellcrank 79, the link arm 81 having one end thereof pivotally connected to the bracket 78 and the other end to the bracket 80 at the fore end of the support rod 9. The bracket 76 is provided with an abutting guide 82 which extends toward the front side of the guide roller 75.

After the support rod 9 is fully inserted in the steel pipe 14 to commence the flaw detecting operation, the cylinder 77 of the guide mechanism is actuated to extend its rod 77A, whereupon the bellcrank 79 is rotated and, in cooperation with the link arm 81, shifts the support frame 74 toward the inner surface of the steel pipe 14, bringing the guide rollers 73A and 73B into abutting contact with the inner surface of the pipe as shown in phantom in FIG. 11. At the same time, the guide roller 75 is caused to abut the inner surface on the opposite side of the steel pipe 14 to support the fore end of the support rod 9 and to hold the window 48 of the support rod 9 in the proximity of the inner surface of the steel pipe 14.

Under these circumstances, the reciprocable rod 51 is operated to raise the base plate 44 toward the inner surface of the steel pipe 14 to contact the respective detector members 46 with the inner surface of the steel pipe 14.

Figure 14:
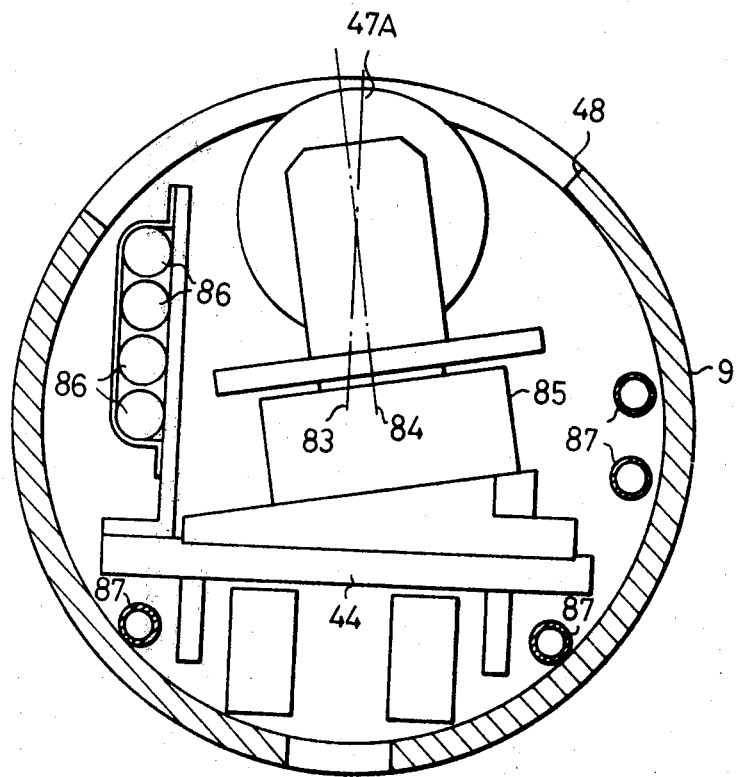
FIG. 14 is a diagrammatic cross-section taken on line XIV—XIV of FIG. 9.

As shown particularly in FIG. 14, the guide roller 47A is supported on a bearing block 85 for rotation about an axis 84 laterally inclined relative to an axis 83 normal to the base plate 44 to follow the helical movement of any pitch along the inner surfaces of the steel pipe 14. When the angle of advancement of the helical movement does not coincide with the direction of the circumferential rotation of the guide roller 47A, there is produced a moment proportional to the product of the angle of inclination of the axis 84 relative to the axis 83 and the radius of the guide roller 47A, causing the direction of the circumferential rotation of the guide roller 47A to coincide with the angle of advancement of the helical movement. In FIG. 14, the reference numeral 86 designates shield wires connected to the magneto-sensitive elements 45 while the reference numeral 87 indicates air pipes for operating the pneumatic cylinder 77. The guide roller 47B is supported in a manner similar to the guide roller 47A to follow the helical movement along the steel pipe 14.

Figure 6:
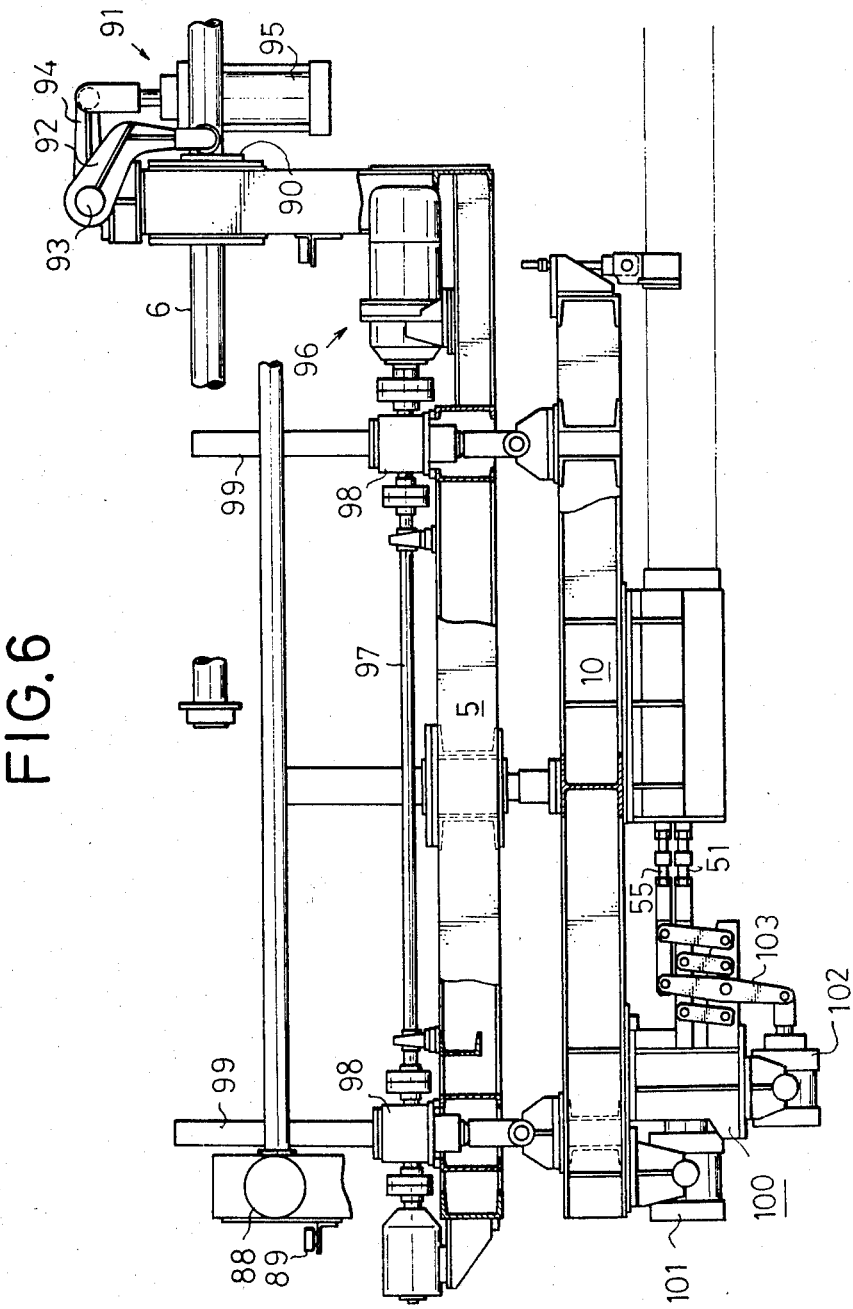
FIG. 6 is a diagrammatic front view of a wheeled carriage for the support rod.
Figure 7:
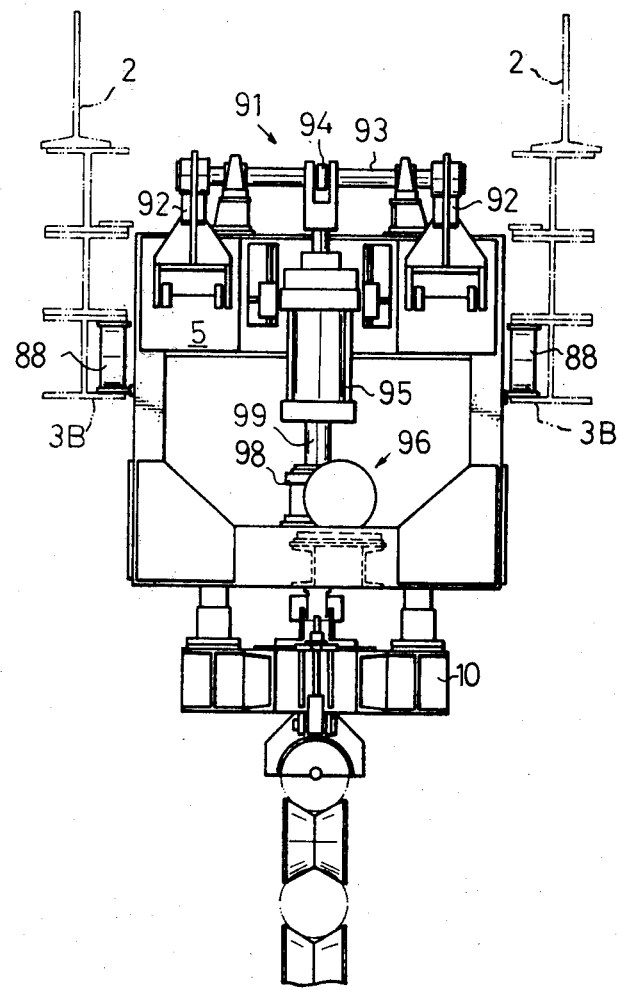
FIG. 7 is a diagrammatic side view of the lift mechanism of FIG. 6.
Figure 8:
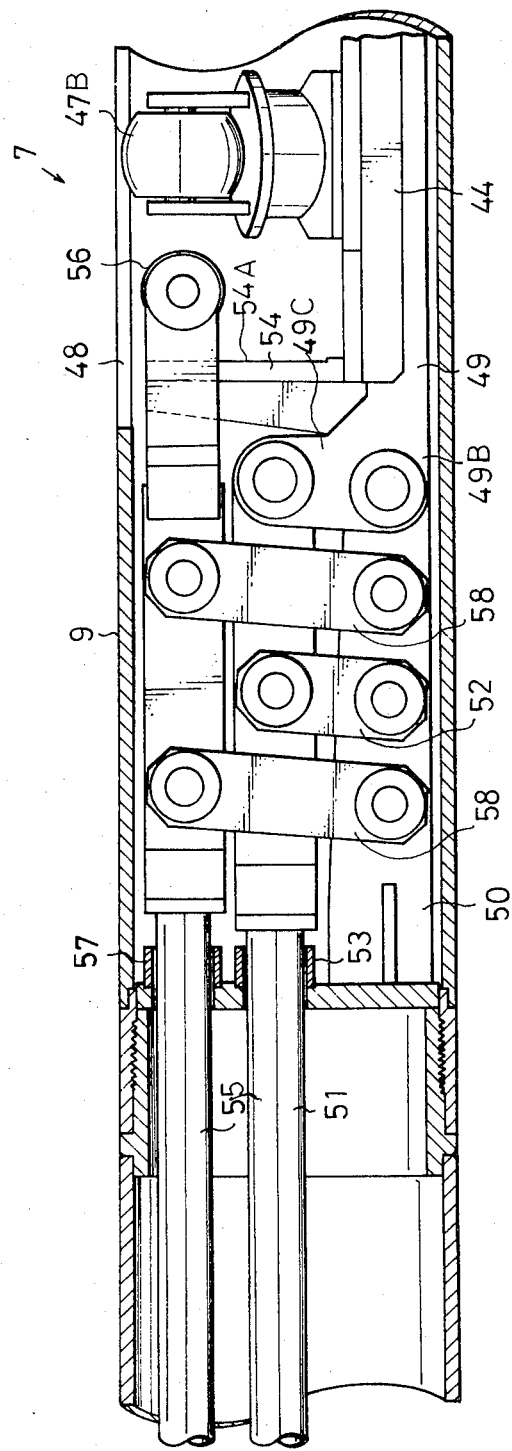
FIGS. 8 through 11 are fragmentary longitudinal cross-sections showing the support rod successively from its base end portion toward its tip end portion.
Figure 9:
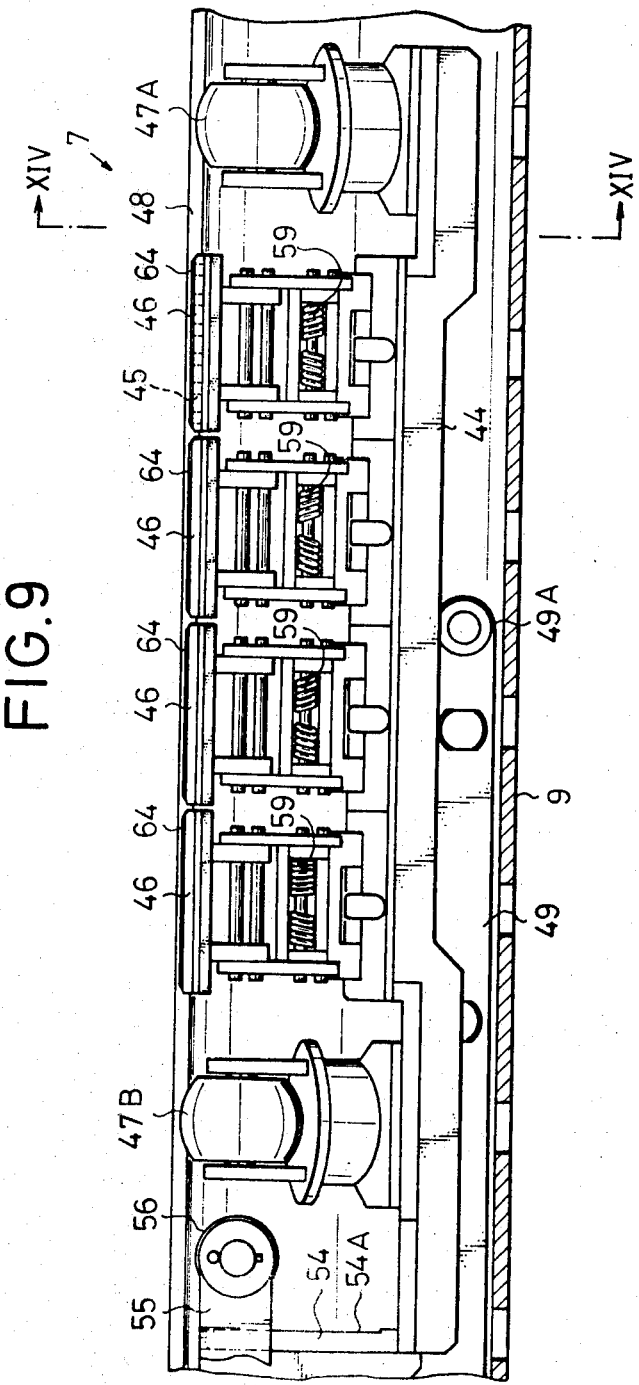
Figure 10:
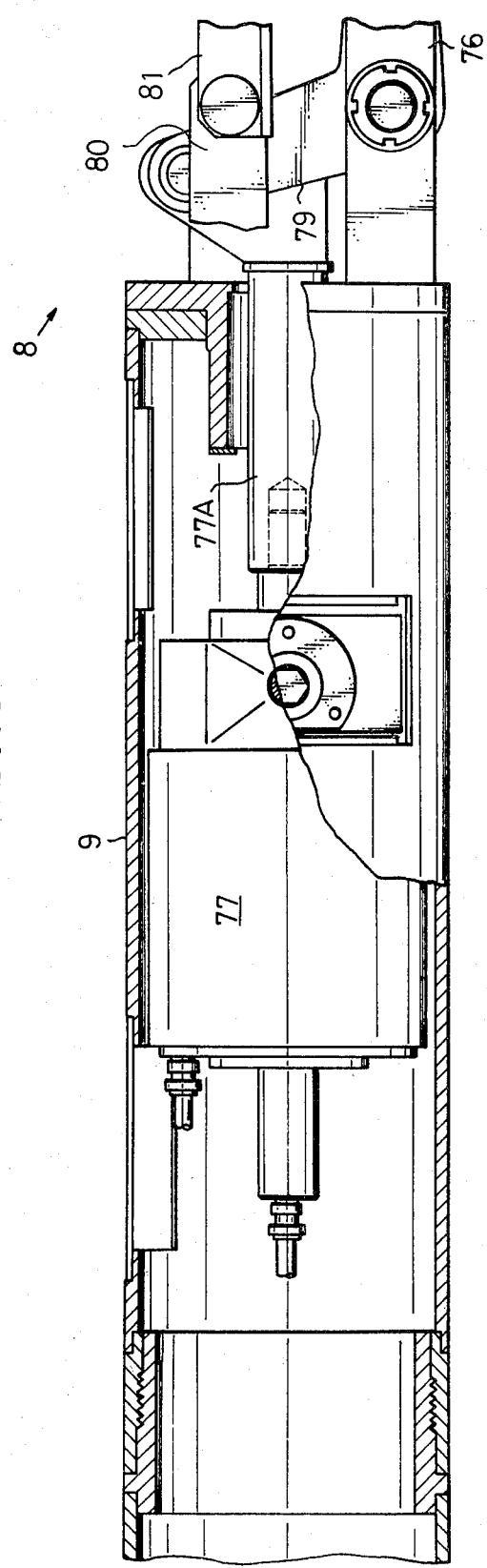

Referring to FIGS. 6 and 7, the carriage 5 is provided with wheels 88 and guide rollers 89. The wheels 88 are placed in the rails 3B while the guide rollers 89 are abutted against the rails 3B to prevent snaking of the carriage 5 while in travel. The carriage 5 is not provided with any automotive means and it is pushingly moved or trailed by the carrige 4 through the connecting rod 6. The fore end of the connecting rod 6 is fitted in the carriage 5 and provided with a collar 90 in abutting engagement with the carriage 5. In other words, the end portion of the connecting rod 6 fitted in the carriage 5 up to the collar 90 to push the carriage 5 by the collar 90 in one way of the travel along the rails 3B. In order to prevent the connecting rod 6 from coming off the carriage 5 during the trailing operation, a holder 91 is mounted on the connecting rod 6, the holder 91 pushing and abutting the collar 90 against the carriage 5 by swing arms 92 which are fixedly mounted at opposite ends of a horizontal rotatable shaft 93. The rotatable shaft 93 is connected to and swung by a cylinder 95 through a crank 94.

A lift mechanism 96 is provided on the carriage 5 to move up and down the support assembly 10 which is suspended therefrom. The lift mechanism 96 is provided with gear boxes 98 which are driven by a common rotational shaft 97, each one of the gear boxes 98 being provided with a pinion (not shown) for meshing engagement with one of the lift rods 99. The lift rods 99 are pivotally connected to the support assembly 10 at the respective lower ends and movable up and down in synchronism with each other to raise or lower the support assembly 10 in the horizontal state.

The support assembly 10 has mounted thereon a rod operating mechanism 100 which operates the reciprocating rod 51 and the base plate support rod 55, including a first cylinder 101 for operating the reciprocating rod 51 and a second cylinder 102 for operating the base plate support plate 55. The cylinder 102 is mounted at a position lower than the cylinder 101 and connected to the base plate support rod 55 through a link 103. The provision of the first and second cylinders 101 and 102 at different levels contributes to reduce the length of the rod operating mechanism 100.

Upon commencing the flaw detection, the support rod 9 is inserted into the steel pipe 14 and then the guide mechanism 8 is operated to bring the detector members 46 into contact with the inner surfaces of the pipe 14. While, the cylinder 17 is operated to lower the magnetizing head assembly 19 along the outer surface of the steel pipe 14 into a position opposing the detector members 46 across the wall of the pipe 14, with the guide rollers 21A and 21B in rolling contact with the outer surfaces of the steel pipe 14 to hold the opposite poles of the exciting magnets 24 close to the outer surfaces of the steel pipe 14. In this manner, the detector members 46 and the exciting magnets 24 are closely opposed each other across the wall of the steel pipe 14. Under these circumstances, the steel pipe 14 is rotated by the turning rollers 16 and at the same time the magnetizing assembly 1 and the detecting end assembly 7 are moved axially in synchronism with each other by gradually extracting the support 9 from the steel pipe 14.

As apparent from the foregoing description, the magnetic flaw detector according to the present invention has the following advantages.

(1) The detecting assembly and the magnetizing assembly are provided separately, inserting the smaller detecting assembly into the steel pipe to be inspected while adapting the bulky magnetizing assembly to run along the outer surfaces of the pipe, so that it becomes possible to conduct the magnetic flow detection on steel pipes of relatively small diameters.

(2) The magnetizing assembly employs DC-excited magnets while the detecting members of the detecting assembly are urged through an window into positions closely opposing the exciting magnets across the wall of the pipe, sufficiently magnetizing the steel pipe up to the inner surface to allow detection of even very fine flaws as well as inspection of thick-walled pipes.

(3) A number of detecting members are aligned in the longitudinal direction of the support rod to perform accurate and efficient flaw detection over the entire area of the inner surface of the pipe.

(4) Each detecting member is urged by suitable biasing means such as a torsion coil spring to let the magneto-sensitive element peep out independently through a window toward the inner surface of the pipe and securely follow the undulations on the inner surface of the pipe to effect flaw detection of high accuracy.

(5) The detector assembly is constructed such that the detecting members are supported by the guide rollers when abutted against the inner wall surface of the pipe, and in turn the detector assembly is supported by the guide rollers of the guide mechanism which are held in rolling contact with the inner wall surface of the pipe, thereby ensuring stable operating conditions.

(6) The magnetizing and detector assemblies are operated in synchronism with each other, and at the same time the exciting magnets are held close the outer wall surface of the pipe, thereby ensuring reliable flaw detecting operation.

(7) The pipe under inspection is put in rotation while the magnetizing and detector assemblies are moved longitudinally along the pipe, so that the scanning for the flaw detection can be effected in a very reliable and simplified manner.

Although preferred embodiments of the invention has been described in detail, it is to be understood that various changes, substitutions and alterations can be made therein without departing from the spirit and scope of the invention as defined by the appended claims.

What is claimed is:

1. A magnetic flaw detector for inspecting inner wall surfaces of a pipe of magnetizable material, comprising:

a support rod mounted on a wheeled carriage which is movable along a rail, said support rod having a hollow space at least in the fore end portion thereof to be inserted into said pipe and a window formed in said fore end portion to open toward an inspecting spot on the inner wall surface of said pipe;

a detector assembly having a base plate accommodated within said hollow space at the fore end of said support rod and movable radially of said support rod, a plural number of detecting members mounted on said base plate in alignment in the longitudinal direction of said support rod, each one of said detecting members having magneto-sensitive element urged by respective biasing means to project independently through said window toward the inner wall surface of said pipe, and a plural number of guide rollers mounted on said base plate and adapted to be brought into rolling contact with the inner wall surface of said pipe to support said base plate when said detecting members are abutted against the inner wall surface of said pipe;

a guide mechanism having a support frame attached to the distal end of said support rod and swingable in a direction opposite to the projecting direction of said magneto-sensitive elements, and a guide roller adapted to be brought into rolling contact with the inner wall surface of said pipe to support said support rod when said support frame is swung out;

a magnetizing assembly having a magnetizing head reciprocably mounted toward and away from the outer surface of said pipe, on a wheeled carriage movable with the first-mentioned wheeled carriage to move said magnetizing head longitudinally along the outer wall surface of said pipe, exciting magnets mounted on said magnetizing head in a position closely opposing said magneto-sensitive elements across the wall of said pipe, and follower rollers adapted to be brought into rolling contact with the outer wall surface of said pipe to support said exciting magnets in an operating position close to the outer wall surface of said pipe; and means for rotating said pipe about the axis thereof during the flaw detecting operation by said detecting and magnetizing assemblies.

2. A magnetic flaw detector as claimed in claim 1, wherein said support rod accommodates therein a reciprocating rod which extends longitudinally of the support rod from the rear end thereof and terminates in said hollow space, and said support rod is provided with a crank member which is positioned in said hollow space, said crank member having a first arm which extends substantially longitudinally of the support rod on the other side of said detector assembly from said window and has two ends, one of which is nearer than the other to the rear end of the support rod, and a second arm which extends transversely of the support rod and has two ends and is connected at one end to said one end of the first arm and is connected at its other end to said reciprocating rod, and said crank member being pivotally connected in the region of said one end of said second arm to the support rod, whereby movement of the reciprocating rod relative to the support rod in the direction away from the fore end of the support rod causes the crank member to pivot in said hollow space to bring said first arm of the crank member into engagement with the detector assembly and urge the detector assembly towards the window, thereby to cause the magnetic-sensitive elements to be projected through said window.

3. A magnetic flaw detector as claimed in claim 1 or 2, wherein said detector assembly has a rear end and a forward end, and is provided at said rear end with a portion which extends transversely of the support rod towards the window, and wherein the support rod accommodates therein an inner rod which extends longitudinally of the support rod from the rear end thereof and terminates in said hollow space at a point forward of the transversely-extending portion of the detector assembly whereat it is provided with abutment means for engaging said transversely-extending portion when the inner rod is moved relative to the support rod in the direction away from the fore end of the support rod thereby to prevent movement of the forward end of the detector assembly into the hollow space, away from the inner wall surface of the pipe.

4. A magnetic flaw detector as claimed in claim 3, wherein said abutment means comprise a roller.

5. A magnetic flaw detector as claimed in claim 3, wherein the base plate of the detector assembly has two ends, one of which is nearer than the other to the rear end of the support rod, and the transversely-extending portion of the detector assembly is a portion of the base plate disposed at said one end thereof.

* * * * *